> United States Patent [19]
> Hacker et al.

[11] Patent Number: 5,650,375
[45] Date of Patent: Jul. 22, 1997

[54] SYNERGISTIC HERBICIDAL COMPOSITIONS

[75] Inventors: Erwin Hacker, Hochheim am Main; Martin Hess, Mainz; Hans-Philipp Huff, Eppstein/Taunus; Hans Schumacher, Flörsheim am Main, all of Germany

[73] Assignee: Hoechst Aktiengesellschaft, Frankfurt, Germany

[21] Appl. No.: 461,718

[22] Filed: Jun. 5, 1995

Related U.S. Application Data

[63] Continuation of Ser. No. 199,667, Feb. 22, 1994, abandoned, which is a continuation of Ser. No. 910,245, Jul. 9, 1992, abandoned.

[30] Foreign Application Priority Data

Jul. 12, 1991 [DE] Germany ............... 41 23 111.2

[51] Int. Cl.$^6$ .................................................. A01N 43/54
[52] U.S. Cl. ...................... 504/136; 504/142; 504/144; 504/145; 504/146
[58] Field of Search ........................ 504/136, 146, 504/130, 139, 156

[56] References Cited

U.S. PATENT DOCUMENTS

| | | | |
|---|---|---|---|
| 2,863,753 | 12/1958 | Wain | 504/309 |
| 3,961,935 | 6/1976 | Satomi et al. | 504/127 |
| 4,460,402 | 7/1984 | Holm | 504/144 |
| 4,690,706 | 9/1987 | Fischer | 504/131 |
| 4,718,937 | 1/1988 | Willms et al. | 544/213 |
| 5,236,887 | 8/1993 | Noveroske | 504/135 |
| 5,478,795 | 12/1995 | Watkins, Jr. | 504/130 |

FOREIGN PATENT DOCUMENTS

| | | |
|---|---|---|
| 587 549 | 12/1987 | Austria . |
| 0 120 578 | 10/1984 | European Pat. Off. . |
| 0 131 258 | 1/1985 | European Pat. Off. . |
| 0 210 818 | 2/1987 | European Pat. Off. . |
| 0 236 273 | 9/1987 | European Pat. Off. . |
| 0 248 968 | 12/1987 | European Pat. Off. . |
| 0 252 237 | 1/1988 | European Pat. Off. . |
| 0 273 668 | 7/1988 | European Pat. Off. . |
| 0 298 901 | 1/1989 | European Pat. Off. . |
| 0 303 383 | 2/1989 | European Pat. Off. . |
| 0 324 302 | 7/1989 | European Pat. Off. . |
| 0 341 011 | 11/1989 | European Pat. Off. . |
| 0 401 677 | 12/1990 | European Pat. Off. . |
| 0 401 678 | 12/1990 | European Pat. Off. . |
| 2 137 092 | 10/1984 | United Kingdom . |
| WO 91/10660 | 7/1991 | WIPO . |

OTHER PUBLICATIONS

The Pesticide Manual (Incorporating The Agrochemicals Handbook), 10th Edition, 1994, pp. 638–644, pp. 271–273.
Blair et al., "A Review of Activity, Fate and Mode of Action of Sulfonylurea Herbicides," Pesticide Science, vol. 22, No. 3 (1988), pp. 195–219.

Chemical Patents Index, Basic Abstracts Journal, Week 8351, Feb. 22, 1984, An 83–847153/51 & JP-A-58 192 808, Nov. 10, 1983.

Chemical Patents Index, Basic Abstracts Journal, Week 8618, Jun. 25, 1986, AN 86–116638/18 & JP-A-61 057 505, Mar. 24, 1986.

Cramp et al., "Design and Synthesis of N–(2,4–difluorophenyl)–2(3–trifluoromethylphenoxy)–3– pyridinecarboxamide (diflufenican), a Novel Pre-and Early Post-Emergence Herbicide for Use in Winter Cereals," Pesticide Science, vol. 18, No. 1 (1987), pp. 15–28.

Devine et al., "Inhibition of Acetolactate Synthase in Susceptible and Resistant Biotypes of Stellaria media," Pesticide Science, vol. 31, No. 3 (1991), pp. 273–280.

O'Sullivan et al., "Chlorsulfuron Reduced Control of Wild Oats (Avena Fatua) with Diclofop, Difenzoquat and Flamprop," Weed Science, vol. 32, No. 3 (1984), pp. 285–289.

Warner, et al., "Tralkoxydim —A New Post–Emergence Cereal Selective Grainicide," Proceedings –British Crop Protection Conference –Weeds (1987), pp. 19–26.

Wightman et al., "The Mode of Action and Basis of Selectivity of Diflufenican in Wheat, Barley and Selected Weed Species," Proceedings –British Crop Protection Conference –Weeds (1985), pp. 171–178.

Zollinger et al., "Antagonism Between Selected Postemergence Herbicides for Grass and Broadleaved Weeds," Proceedings of the Western Society of Weed Science, vol. 37 (1984), pp. 167–171.

The Agrochemicals Handbook, 2nd edition, The Royal Society of Chemistry, Nottingham, England, 1987, p. A926.

Primary Examiner—José G. Dees
Assistant Examiner—Brian Bembenick
Attorney, Agent, or Firm—Curtis, Morris & Safford, P.C.

[57] ABSTRACT

The invention relates to herbicidal compositions which comprise

A) a compound of the formula I or salts thereof $$H_3C-SO_2 \diagdown N-SO_2-NH-CO-NH-\text{pyrimidine}(OCH_3)_2 \quad (I)$$
$$H_3C \diagup$$

in combination with

B) one or more compounds selected from the group comprising growth-regulator-type herbicides, dicamba and its salts, diflufenican, nitrodiphenyl ethers, sulfonylureas which differ from that of the formula (I) and their salts, and selective grass herbicides.

They are particularly suitable for selectively controlling weeds in rice, soya and other crops.

9 Claims, No Drawings

SYNERGISTIC HERBICIDAL COMPOSITIONS

This application is a continuation of application Ser. No. 08/199,667 abandoned, filed Feb. 22, 1994, which is a continuation of application Ser. No. 07/910,245 filed Jul. 9, 1992 abandoned.

The invention is in the field of the crop protection agents which can be employed against monocotyledon and dicotyledon weeds, in particular in the combination of herbicides.

The action of an individual herbicide used in acceptable application rates is frequently insufficient for controlling the spectrum of monocotyledon and dicotyledon weeds which exists in agricultural practise. To allow the grower to control the weed spectrum in cereals, maize and other crops with one or a few application(s) of herbicidal active substances, it is sometimes more suitable to use combinations of a variety of active substances.

Combinations of herbicides have now been found whose action, surprisingly, exceeds the extent which would have been expected taking into account the individual action of the components. The combinations of herbicides, according to the invention, therefore allow a surprisingly great reduction in application rate of each of the components.

The invention therefore relates to herbicidal compositions which comprise

A) a compound of the formula I or salts thereof

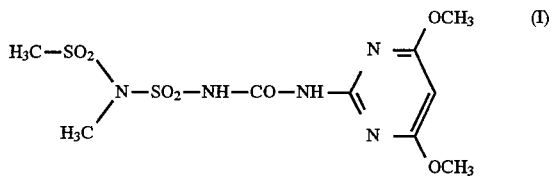

in combination with

B) one or more compounds selected from the group comprising growth-regulator-type herbicides, dicamba and salts thereof, diflufenican, nitrodiphenyl ethers, sulfonylureas which differ from the urea of the formula (I), and salts thereof, and selective grass herbicides.

The compound of the formula (I) is known as amidosulfuron and disclosed in EP-A-0,131,258 (U.S. Pat. No. 4,718,937).

Amidosulfuron is a herbicidal active substance from the group comprising the sulfonylureas and is generally applied pre- and post-emergence in cereals, rice and maize at application rates of 5–120 g of a.i./ha, controlling a broad spectrum of annual and perennial broad-leaf weeds and Cyperaceae (g of a.i./ha=gram per hectare based on active ingredient). For use, the active substance is generally formulated as a WP (water-soluble powder) or WDG (water-dispersible granules) and employed in the customary manner in the form of a dilution with water.

Particularly suitable growth-regulator-type herbicides are the following:
a) MCPB i.e. 4-(4-chloro-2-methylphenoxy)butanoic acid or salts thereof (for example the sodium salt);
b) mecoprop i.e. 2-(4-chloro-2-methylphenoxy)propionic acid or salts thereof; in the form of a racemic mixture or as the (R)-isomer (mecoprop-P);
c) 2,4-D i.e. 2-(2,4-dichlorophenoxy)acetic acid or salts thereof or esters thereof;
d) 2,4-DB i.e. 4-(2,4-dichlorophenoxy)butanoic acid or salts thereof;
e) dichlorprop i.e. 2-(2,4-dichlorophenoxy)propionic acid or salts thereof or esters thereof.
f) MCPA i.e. 2-(4-chloro-2-methylphenoxy)acetic acid or salts thereof.

The abovementioned compounds a) to f) represent standard herbicides which are used post-emergence in a large number of agriculturally used crops for controlling weeds and Cyperaceae. Application rates of 100–3000 g of a.i./ha as individual active substances cover in each case a specific sector of the weed flora. The various compounds are used in the forms of the salts and/or esters (references: cf. "The Pesticide Manual", British Crop Protection Council, 9th Edition 1991 and references cited therein).

Dicamba, i.e. 3,6-dichloro-2-methoxybenzoic acid (or the salts thereof and esters thereof), is also a widely used herbicidal active substance which is applied analogously to the growth-regulator herbicides. The active substance is mainly used post-emergence (for example, inter alia, in cereals and maize), likewise in the forms of the salts thereof and/or esters thereof (cf. "The Pesticide Manual", already mentioned above).

Diflufenican, i.e. N-(2,4-difluorophenyl)-2-[3-(trifluoromethyl)phenoxy]pyridine-3-carboxamide, is employed pre- and post-emergence for controlling weeds in cereals and other crops at a rate of 50–500 g of a.i./ha. It is marketed mostly in the form of finished formulations together with other herbicidal active substances (cf. "The Pesticide Manual", already mentioned above).

Particularly suitable nitrodiphenyl ethers are the following:
a) bifenox, i.e. methyl 5-(2,4-dichlorophenoxy)-2-nitrobenzoate; application rate 50–1000 g of a.i./ha when used as single active substance pre- and post-emergence, for example in cereals, rice and maize.
b) fluorglycofen, i.e. carboxymethyl 5-[2-chloro-4-(trifluoromethyl)phenoxy]-2-nitrobenzoate; application as single active substance for example only 5–50 g of a.i./ha pre- and post-emergence in cereals and soya.
c) acifluorfen, i.e. 5-[2-chloro-4-(trifluoromethyl)-phenoxy]-2-nitrobenzoic acid or salts thereof; application as single active substance for example at a rate of 100–500 g of a.i./ha pre- and post-emergence in soya and cereals.
d) oxyfluorfen, i.e. 5-[2-chloro-4-(trifluoromethyl)-phenoxy]-1-ethoxy-2-nitrobenzene; application as single active substance for example at a rate of 100–1000 g of a.i./ha pre- and post-emergence in soya or on areas not under cultivation.
e) lactofen, i.e. 1-(ethoxycarbonyl)ethyl 5-[2-chloro-4-(trifluoromethyl)phenoxy]-2-nitrobenzoate; application as single active substance for example at a rate of 50–500 g of a.i./ha pre- and post-emergence in soya and cereals.
f) fomesafen, i.e. N-methylsulfonyl-5-[2-chloro-4-(trifluoromethyl)phenoxy]-2-nitrobenzamide; application as single active substance for example at a rate of 50–1000 g of a.i./ha pre- and post-emergence in soya or cereals.

All of the nitrophenyl ethers mentioned are described in "The Pesticide Manual" (already mentioned above).

Particularly suitable sulfonylureas are the following:
a) sulfonylureas which are employed mainly in cereals, in some cases in potatoes and in grassland for post-emergence control of broad-leaf and grass weeds (for example at a rate of 5–80 g of a.i./ha), for example
  aa) triasulfuron, i.e. 1-[2-(2-chloroethoxy)-phenylsulfonyl]-3-(4-methoxy-6-methyl-1,3,5-triazin-2-yl)-urea;
  ab) chlorsulfuron, i.e. 1-(2-chlorophenylsulfonyl)-3-(4-methoxy-6-methyl-1,3,5-triazin-2-yl)-urea;
  ac) tribenuron or tribehuron-methyl, i.e. 1-[2-(carboxy- or methoxycarbonyl)phenylsulfonyl]-3-methyl-3-(4-methoxy-6-methyl-1,3,5-triazin-2-yl)-urea;

ad) thifensulfuron or thifensulfuron-methyl, i.e. 1-[2-(carboxy- or methoxycarbonyl)-thiophen-3-yl-sulfonyl]-3-(4-methoxy-6-methyl-1,3,5-triazin-2-yl)-urea and b) sulfonylureas which are employed mainly in maize and perennial crops for post-emergence control of grass and broad-leaf weeds (5–80 g of a.i./ha), for example ba) nicosulfuron, i.e. 1-[3-(dimethylamino-carbonyl)-pyridin-2-yl-sulfonyl]-3-(4,6-dimethoxypyrimidin-2-yl)-urea;

bb) primisulfuron or primisulfuron-methyl, i.e. 1-[2-(carboxy- or methylcarbonyl)-phenyl-sulfonyl]-3-[4,6-bis(difluoromethoxy)-pyrimidin-2-yl]-urea;

bc) DPX-E 9636, i.e. 1-[3-(ethylsulfonyl)-pyridin-2-yl-sulfonyl]-3-(4,6-dimethoxypyrimid-2-yl)-urea;

bd) pyridylsulfonylureas as they are described in PCT Patent Application PCT/EP 90/02308 (WO 91/10660), preferably those of the formula A1 or salts thereof

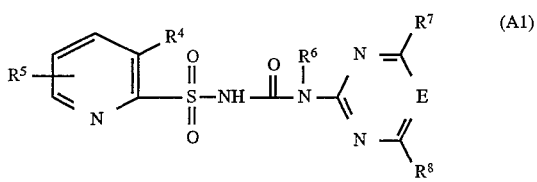

in which
E is CH or N, preferably CH,
$R^4$ is iodine or $NR^9R^{10}$,
$R^5$ is E, halogen, cyano, $C_1$–$C_3$-alkyl, $C_1$–$C_3$-alkoxy, $C_1$–$C_3$-haloalkyl, $C_1$–$C_3$-haloalkoxy, $C_1$–$C_3$-alkylthio, ($C_1$–$C_3$-alkoxy)-$C_1$–$C_3$-alkyl, ($C_1$–$C_3$-alkoxy)-carbonyl, mono- or di-($C_1$–$C_3$-alkyl)-amino, $C_1$–$C_3$-alkyl-sulfinyl or -sulfonyl, $SO_2$—$NR^aR^b$ or $CO$—$NR^aR^b$, in particular H,
$R^a$ and $R^b$, independently of one another are H, $C_1$–$C_3$-alkyl, $C_1$–$C_3$-alkenyl, $C_1$–$C_3$-alkynyl, or together are —$(CH_2)_4$—, —$(CH_2)_5$— or —$(CH_2)_2$—O—$(CH_2)_2$—,
$R^6$ is H or $CH_3$,
$R^7$ is halogen, $C_1$–$C_2$-alkyl, $C_1$–$C_2$-alkoxy, $C_1$–$C_2$-haloalkyl, preferably $CF_3$, $C_1$–$C_2$-haloalkoxy, preferably $OCHF_2$ or $OCH_2CF_3$,
$R^8$ is $C_1$–$C_2$-alkyl, $C_1$–$C_2$-haloalkoxy, preferably $OCHF_2$ or $C_1$–$C_2$-alkoxy, and
$R^9$ is $C_1$–$C_4$-alkyl and $R^{10}$ is $C_1$–$C_4$-alkylsulfonyl, or $R^9$ and $R^{10}$ together are a chain of the formula —$(CH_2)_3SO_2$— or —$(CH_2)_4SO_2$—.

The herbicides mentioned above under aa) to ba) are described in "The Pesticide Manual" (already mentioned above).

Primisulfuron and primisulfuron-methyl are known from Brighton Crop Protection Conference—Weeds—1987, p. 41–48.

DPX-E 9636 is known from Brighton Crop Protection Conference—Weeds—1989, p. 33 et seq.

Suitable grass herbicides are mainly the following herbicides for the selective post-emergence control of harmful plants (grass weeds and broad-leaf weeds) in cereals (range of application rates 30 to 1000 g of a.i./ha):

a) diclofop or diclofop-methyl, i.e. 2-[4-(2,4-dichlorophenoxy)phenoxy]propionic acid or its methyl ester;

b) tralkoxydim, i.e. 2-[1-(ethoxyimino)-propyl]-3-hydroxy-5-mesitylcyclohex-2-en-1-one;

c) difenzoquat, i.e. 1,2-dimethyl-3,5-diphenylpyrazolium salts;

d) imazamethabenz, i.e. a mixture of 6-(4-isopropyl-4-methyl-5-oxo-2-imidazolin-2-yl)-3-methyl-benzoic acid and -4-methyl-benzoic acid or their methyl esters;

e) flamprop or flamprop-methyl, i.e. N-benzoyl-N-(3-chloro-4-fluorophenyl)-alanine, or its methyl ester;

f) CGA-184927, i.e. propargyl (2R)-2-[4-(5-chloro-3-fluoropyridin-2-yloxy)-phenoxy]-propionate.

The last-mentioned compounds a) to e) are likewise described in "The Pesticide Manual" (see above).

CGA-184927 is known from EP-A-191,736 and Brighton Crop Protection Conference—Weeds—1989.

Surprisingly, it has emerged that superadditive (=synergistic) effects occurred when amidosulfuron was used together with one or more active substances from group B. The action in the combinations was greater than that of the single products used on their own. These effects allow the application rate to be reduced, a broad spectrum of broad-leaf weeds and grass weeds to be controlled, a more rapid action, a prolonged long-term action, a complete control of the harmful plants with only one, or few, applications, and a widening of the potential application period when the active compounds are combined. These properties are required for practical weed control to keep agricultural crops free from undesired competitive plants and thus to guarantee the quality and quantity of the yields and/or to increase them. These novel combinations markedly outperform the state of the art with regard to the properties described.

The choice of the ratio by weight and the application rates are a function of, for example, the other component in the mixture, the development stage of the broad-leaf weeds or grass weeds, the weed spectrum, environmental factors and climatic conditions.

The ratios by weight A:B of the combined herbicides can therefore vary within wide limits and are generally 1:200 to 20:1.

The following ratios by weight are preferably used:

In the case of combinations of the compounds of the formula (I) or salts thereof with growth-regulator herbicides: 1:200 to 2:1, preferably 1:50 to 1:1;

with dicamba: 1:200 to 2:1, preferably 1:50 to 1:1;

with diflufenican: 1:200 to 5:1, preferably 1:50 to 2:1;

with nitrodiphenyl ethers: 1:200 to 10:1, preferably 1:50 to 5:1;

with sulfonylureas: 1:16 to 20:1, preferably 1:10 to 20:1;

with grass herbicides: 1:200 to 3:1, preferably 1:50 to 10:1.

The application rates of the herbicide A in the active substance combinations are preferably between 5 and 100 g of a.i./ha (a.i.=relative to active ingredient). The application rates of B type compounds in the mixtures are generally from 5 to 100 g of a.i./ha, preferably with growth-regulator herbicides: 50 to 1000 g of a.i./ha, with dicamba: 50 to 1000 g of a.i./ha, with diflufenican: 20 to 1000 g of a.i./ha, with nitrodiphenyl ethers: 10 to 1000 g of a.i./ha, with sulfonylureas: 5 to 80 g of a.i./ha, with grass herbicides: 30 to 1000 g of a.i./ha.

The active substance combinations according to the invention can exist as mixed formulations of the two components which are then applied in the customary manner in the form of a dilution with water, or are prepared in the form of so-called tank mixes by concomitant dilution of the separately formulated components with water.

The A type and B type compounds or their combinations can be formulated in many ways, depending on the prevailing biological and/or chemicophysical parameters. The following are possible exemplary formulations: wettable powders (WP), emulsifiable concentrates (EC), aqueous solutions (SL), emulsions (EW) such as oil-in-water and water-in-oil emulsions, sprayable solutions or emulsions, dispersions on an oil or water basis, suspoemulsions, dusting powders (DP), seed-dressing agents, granules for soil application or for broadcasting, or water-dispersible granules (WG), ULV formulations, micro-capsules or waxes.

The individual formulation types are known in principle and are described, for example, in: Winnacker-Küchler, "Chemische Technologie [Chemical Technology]", Volume 7, C. Hauser Verlag Munich, 4th Ed. 1986; van Valkenburg, "Pesticides Formulations", Marcel Dekker N.Y., 1973; K. Martens, "Spray Drying Handbook", 3rd Ed. 1979, G. Goodwin Ltd. London.

The formulation auxiliaries required such as inert materials, surfactants, solvents and other additives are equally known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry"; 2nd Ed., J. Wiley & Sons, N.Y. Marsden, "Solvents Guide", 2nd Ed., Interscience, N.Y. 1950; McCutcheon's, "Detergents and Emulsifiers Annual", MC Publ. Corp., Ridegewood N.J.; Sisley and Wood, "Encyclopedia of Surface Active Agents", Chem. Publ. Co. Inc., N.Y. 1964; Schönfeldt, "Grenzfl ächenaktive Äthylenoxidaddukte [Surface-active Ethylene Oxide Adducts]", Wiss. Verlags-gesellschaft, Stuttgart 1976, Winnacker-Küchler, "Chemische Technologie [Chemical Technology]", Volume 7, C. Hauser Verlag Munich, 4th Ed. 1986.

Based on these formulations, it is also possible to prepare combinations with other pesticidally active substances such as other herbicides, fungicides or insecticides, as well as safeners, fertilizers and/or growth regulators, for example in the form of a finished formulation or a tank mix.

Wettable powders are preparations which can be dispersed uniformly in water and which comprise, beside the active substance, ionic or non-ionic surfactants (wetting agents, dispersants), for example polyoxethylated alkylphenols, polyethoxylated fatty alcohols or fatty amines, fatty alcohol polyglycol ether sulfates, alkanesulfonates or alkylbenzenesulfonates, sodium ligninsulfonate, sodium 2,2'-dinaphthylmethane-6,6'-disulfonate, sodium dibutyl-naphthalenesulfonate or else sodium oleoylmethyltaurinate, besides a diluent or inert substance.

Emulsifiable concentrates are prepared by dissolving the active substance in an organic solvent, for example butanol, cyclohexanone, dimethylformamide, xylene, or else higher-boiling aromatics or hydrocarbons, with the addition of one or more ionic or non-ionic surfactants (emulsifiers). The following are examples of emulsifiers which can be used: calcium alkylarylsulfonates such as calcium dodecylbenzenesulfonate, or non-ionic emulsifiers such as fatty acid polyglycol esters, alkylaryl polyglycol ethers, fatty alcohol polyglycol ethers, propylene oxide/ethylene oxide condsensation products, alkyl polyethers, sorbitan fatty acid esters, polyoxyethylene sorbitan fatty acid esters or polyoxethytene sorbitol esters.

Dusting powders are obtained by grinding the active substance with finely divided solid substances, for example talc, natural clays such as kaolin, bentonite and pyrophyllite, or diatomaceous earth.

Granules can be prepared either by spraying the active substance onto adsorptive, granulated inert material or by applying active substance concentrates to the surface of carrier substances such as sand, kaolinites or granulated inert material with the aid of adhesives, for example polyvinyl alcohol, sodium polyacrylate or else nineral oils. Suitable active substances can also be granulated in the fashion customary for the preparation of fertilizer granules, if desired in the form of a mixture with fertilizers. Water-dispersible granules are generally prepared by methods such as spray-drying, fluidized-bed granulation, disk granulation, mixing with high-speed mixers and extrusion without solid inert material.

As a rule, the agrochemical preparations comprise 0.1 to 99% by weight, in particular 2 to 95% by weight, of active substances of types A+B. The concentrations of the active substances A+B can differ in the formulations.

For example, the active substance concentration in wettable powders is approximately 10 to 95% by weight, the remainder to 100% by weight is composed of customary formulation components. In the case of emulsifiable concentrates, the active substance concentration can be approximately 1 to 85% by weight, preferably 5 to 80% by weight. Formulations in the form of dusts comprise approximately 1 to 25% by weight, usually 5 to 20% by weight, of active substance, sprayable solutions approximately 0.2 to 25% by weight, preferably 2 to 20% by weight, of active substance. In the case of granules such as dispersible granules, the active substance content depends partly on whether the active compound is liquid or solid and on which granulation auxiliaries and fillers are used. The content in the case of the water-dispersible granules is generally between 10 and 90% by weight.

Besides, the active substance formulations mentioned optionally comprise the adhesives, wetting agents, dispersants, emulsifiers, penetrants, preservatives, antifreeze agents and solvents, fillers, colorants and carriers, defoamers, evaporation inhibitors, pH regulators and viscosity regulators which are customary in each case.

For use, the formulations which exist in commercially available form are optionally diluted in the customary manner, for example using water in the case of wettable powders, emulsifiable concentrates, dispersions and water-dispersible granules. Preparations in the form of dusts, granules for soil application or for broadcasting as well as sprayable solutions are customarily not diluted further with other inert substances before application.

The active substances can be applied to the plants, parts of the plants, seeds of the plants or the area under cultivation.

The active substances are preferably applied jointly in the form of tank mixes, the optimally formulated concentrated formulations of the single active substances being mixed concomitantly with water in the tank, and the spray mixture obtained is applied.

The examples which follow are intended to illustrate the invention:

A. FORMULATION EXAMPLES a) A dusting agent is obtained by mixing 10 parts by weight of an active substance combination according to the invention and 90 parts by weight of talc as inert substance and comminuting the mixture in a hammer mill.

b) A wettable powder which is readily dispersible in water is obtained by mixing 25 parts by weight of active substances A+B, 64 parts by weight of kaolin-containing quartz as inert substance, 10 parts by weight of potassium ligninsulfonate and 1 part by weight of sodium oleoylmethyltaurate as wetting and dispersing agent, and grinding the mixture in a pinned disk mill.

c) A dispersion concentrate which is readily dispersible in water is obtained by mixing 20 parts by weight of active substances A+B with 6 parts by weight of alkylphenol polyglycol ether (®Triton X 207), 3 parts by weight of isotridecanol polyglycol ether (8 EO) and 71 parts by weight of paraffinic mineral oil (boiling range, for example, approx. 255° to 277° C.), and grinding the mixture in a ball mill to a fineness of below 5 microns.

d) An emulsifiable concentrate is obtained from 15 parts by weight of cyclohexanone as solvent and 10 parts by weight of oxethylated nonylphenol as emulsifier.

e) Water-dispersible granules are obtained by mixing 75 parts by weight of active substances A+B, 10 parts by weight of calcium ligninsulfonate, 5 parts by weight of sodium lauryl sulfate, 3 parts by weight of polyvinyl alcohol and 7 parts by weight of kaolin, grinding the mixture on a pinned disk mill and granulating the powder in a fluidized bed by spraying on water as granulation liquid.

f) Alternatively, water-dispersible granules are obtained by homogenizing and precomminuting 25 parts by weight of active substances A+B, 5 parts by weight of sodium2,2'-dinaphthylmethane-6,6'-disulfonate, 2 parts by weight of sodium oleoylmethyltaurate, 1 part by weight of polyvinyl alcohol, 17 parts by weight of calcium carbonate and 50 parts by weight of water on a colloid mill, subsequently grinding the mixture on a bead mill, and atomizing and drying the resulting suspension in a spray tower by means of a single-substance nozzle.

B. BIOLOGICAL EXAMPLES

Various economically important broad-leaf weeds and grass weeds had grown under natural field conditions (field trials). The herbicide mixtures were applied in the 2- to 5-leaf stage of the crop plants and the harmful plants by means of plot spray equipment. The water application rate was 300–400 liters of water per hectare.

Within 4 weeks after the application, the herbicidal activity of the treated plots was assessed by comparison with untreated control plots by visual scoring. The herbicidal action as regards influencing the plant growth and chlorotic and necrotic effects up to the total destruction of the weeds was assessed qualitatively and quantitatively and indicated as percentage action (0–100%).

The results are compiled in Tables 1 and 2 below:

TABLE 1

| Active substance(s) | | % control | | | % damage |
|---|---|---|---|---|---|
| | g of a.i./ha | ARCCA | EMEAU | CHEAL | HORVS |
| A Compound (I) | 30 | 4 | 39 | 67 | 0 |
| | 45 | 5 | 57 | 83 | 0 |
| | 60 | 6 | 69 | 92 | 0 |
| B MCPA | 200 | 20 | 10 | 3 | 0 |
| | 420 | 40 | 15 | 10 | 0 |
| | 560 | 60 | 30 | 60 | 0 |
| A + B | 30 + 200 | 79 | 77 | 71 | 0 |
| | 30 + 420 | 93 | 95 | 98 | 0 |

ARCCA = *Arctotheca calendula*
EMEAU = *Emex australis*
CHEAL = *Chenopodium album*
HORVS = *Hordeum vulgare* (spring barley)
Compound (I) = amidosulfuron

TABLE 2

| Active substance(s) | | % control | | | | % damage |
|---|---|---|---|---|---|---|
| | g of a.i./ha | AMARE | BRANA | POLCO | CHEAL | HORVS |
| A = compound (I) | 30 | 50 | 67 | 76 | 67 | 0 |
| | 45 | 75 | 83 | 78 | 83 | 0 |
| | 60 | 89 | 92 | 85 | 92 | 0 |
| B1 = 2,4-D | 210 | 20 | 23 | 12 | 18 | 0 |
| | 420 | 38 | 33 | 18 | 21 | 0 |
| | 840 | 65 | 80 | 30 | 60 | 0 |
| B2 = dicamba | 110 | 30 | 29 | 10 | 12 | 0 |
| | 220 | 43 | 30 | 15 | 20 | 0 |
| A + B1 | 30 + 210 | 90 | 95 | 95 | 90 | 0 |
| | 30 + 420 | 95 | 100 | 96 | 100 | 0 |
| A + B2 | 30 + 110 | 85 | 100 | 85 | 100 | 0 |
| | 30 + 220 | 95 | 100 | 85 | 100 | 0 |

AMARE = *Amaranthus retroflexus*
BRANA = *Brassica napus*
POLCO = *Polygonum convolvulus*
CHEAL = *Chenopodium album*
HORVS = *Hordeum vulgare*
Compound (I) = amidosulfuron The examples in the Tables show that only high dosage rates of the single active substances allow good control of individual weeds. The components in the mixtures, applied at low dosage rates, only show poor activity, far less than required in practise. The concomitant use of the active substances allow good effects to be achieved on all test weed species. The additive action of the individual components was markedly exceeded (synergism), i.e. the control level required is achieved by markedly lower application rates. These effects broaden the spectrum of action.

The crop tolerance, assessed in the form of damage, is not adversely affected, i.e. the combinations can be judged as fully selective.

We claim:

1. A herbicidal composition which comprises

A) a compound of the formula I or salts thereof

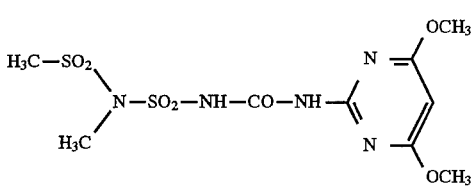

(I)

in combination with

B) one or more growth-regulator herbicides and analogous compounds selected from the group consisting of MCPB, mecoprop, 2,4-D, 2,4-DB, dichlorprop, MCPA and dicamba.

2. A herbicidal composition which comprises

A) a compound of the formula I or salts thereof

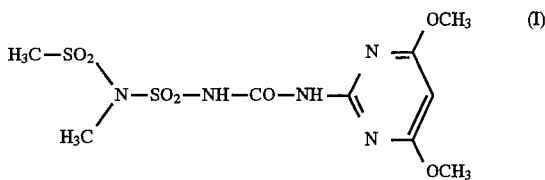

(I)

in combination with

B) one or more growth-regulator herbicides and analogous compounds selected from the group consisting of MCPA, dichlorprop, 2,4-D, and mecoprop.

3. A composition as claimed in claim 1, which comprises the compound (I) or salts thereof and the compounds selected from group B in a ratio by weight of 1:200 to 20:1.

4. A composition as claimed in claim 1, which comprises, besides the active substances of type A or B, customary formulation auxiliaries.

5. A method of controlling undesired plants, which comprises applying a herbicidally effective amount of a combination of active substances A+B as defined in claim 1 to these plants or to the area under cultivation.

6. The method as claimed in claim 5, wherein the application rates of the compounds of the formula (I) or salts thereof are from 5 to 100 g/ha and the application rates of the B type compounds are from 5 to 1000 g/ha.

7. The method as claimed in claim 5, wherein the active substances of types A and B are applied in a ratio by weight of 1:200 to 20:1.

8. The method as claimed in claim 6, wherein the active substances of types A and B are applied in a ratio by weight of 1:200 to 20:1.

9. The method as claimed in claim 5, wherein harmful plants in crops of useful plants are controlled selectively.

* * * * *